United States Patent [19]

Naylor

[11] 4,219,772
[45] Aug. 26, 1980

[54] APPARATUS FOR NONDESTRUCTIVE TESTING OF SMALL BLIND BORES UTILIZING THE DRY MAGNETIC PARTICLE METHOD

[75] Inventor: Carl A. Naylor, York, Pa.
[73] Assignee: Allis-Chalmers Corporation, Milwaukee, Wis.
[21] Appl. No.: 927,772
[22] Filed: Jul. 25, 1978
[51] Int. Cl.² .......................................... G01R 33/00
[52] U.S. Cl. ..................................... 324/216; 324/263
[58] Field of Search .............................. 324/214-216, 324/228, 232, 235, 239, 240-243, 64

[56] References Cited
U.S. PATENT DOCUMENTS

| | | | |
|---|---|---|---|
| 2,440,044 | 4/1948 | Greenslade | 324/64 |
| 2,587,476 | 2/1952 | Huhn | 324/216 |
| 2,682,032 | 5/1954 | Dehn et al. | 324/216 |

OTHER PUBLICATIONS

"Magnetic Particle Testing of Commercial Forgings," pp. 7, 8, 11, 13, 14, 17, Forging Manufacturer's Assoc. Inc., 1944.

Primary Examiner—Rudolph V. Rolinec
Assistant Examiner—Walter E. Snow
Attorney, Agent, or Firm—Robert C. Jones

[57] ABSTRACT

A pair of electrical prods along with a powder supply gun are incorporated in a single portable frame member which is easily insertable into a relatively small blind bore; prod tension against the bore wall is adjustable by varying spring plunger tension; incorporated in the apparatus is the ability to locate indications in all directions by provision of both linear and axial heads which interchange on the same frame or handle; powder is applied to the area to be inspected while current is flowing into the prods, and the powder gun can be rotated and retracted as required to provide full coverage of the area to be inspected with powder.

11 Claims, 8 Drawing Figures

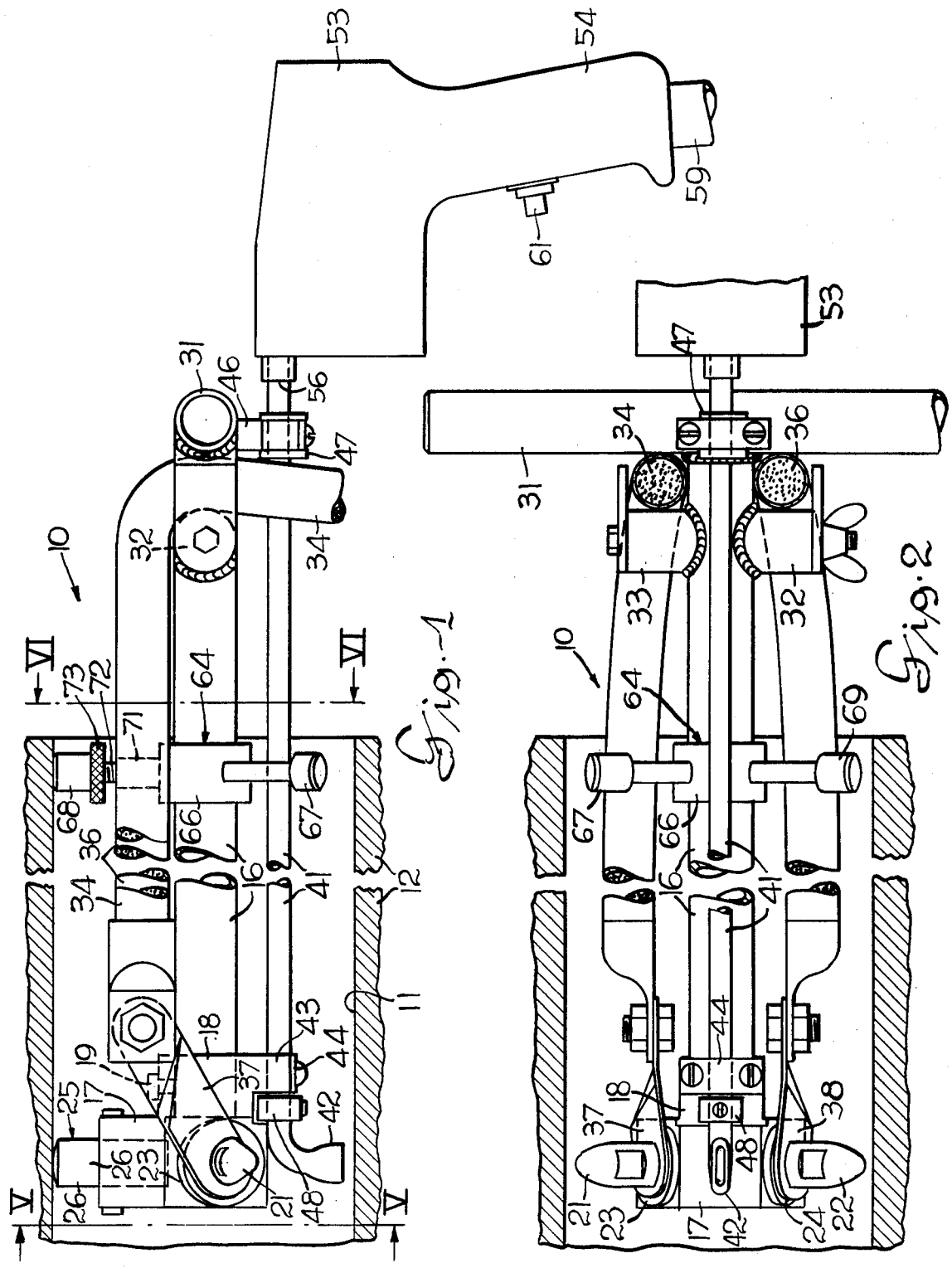

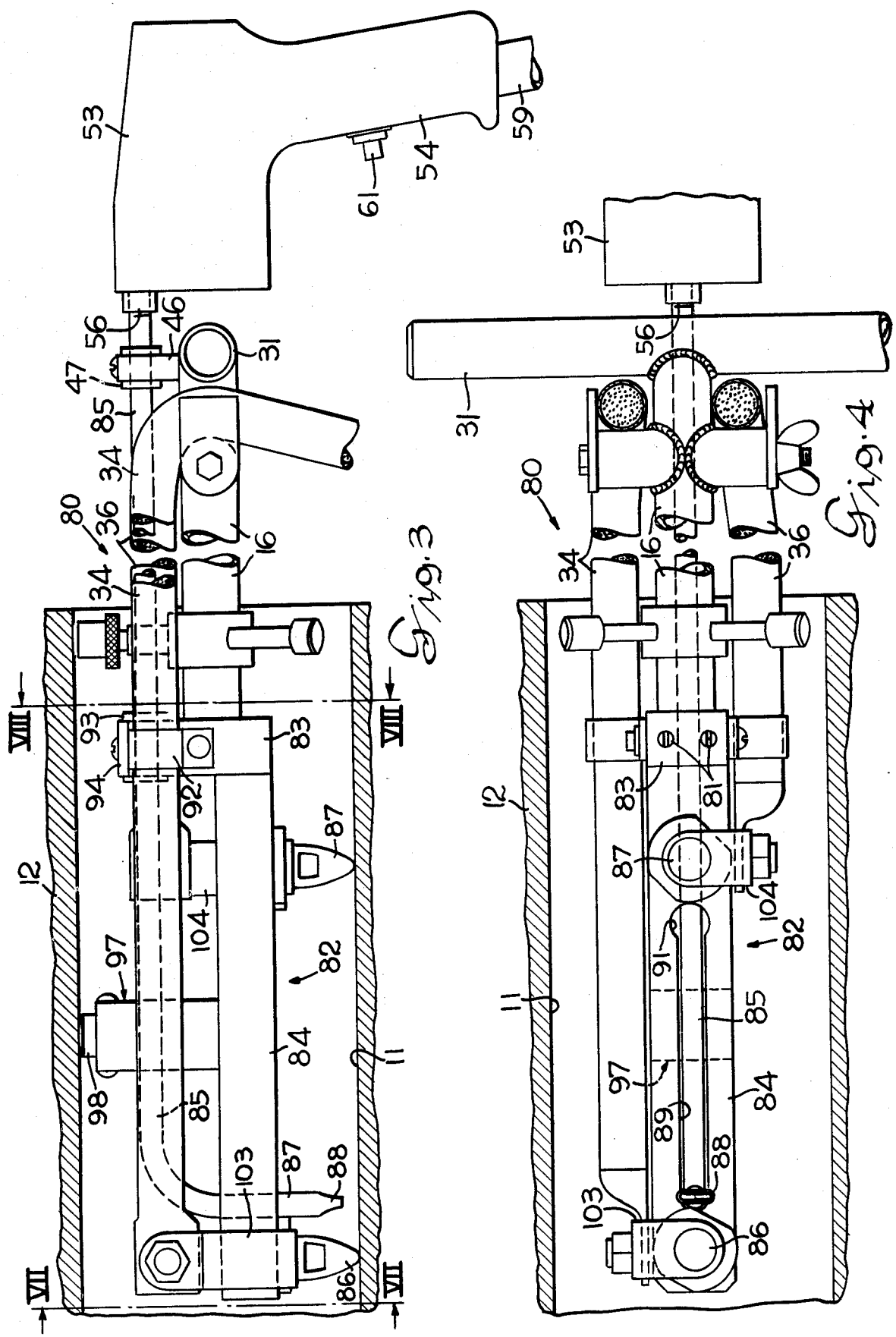

APPARATUS FOR NONDESTRUCTIVE TESTING OF SMALL BLIND BORES UTILIZING THE DRY MAGNETIC PARTICLE METHOD

BACKGROUND OF THE INVENTION

The invention relates to an improvement in apparatus for nondestructive testing of base metal, welds and localized repair areas utilizing a dry magnetic particle method.

Equipment fabricated for nuclear requirements or for other highly specialized requirements demands that base metals, welds and localized repair areas be inspected for continuity of material for insuring the integrity of the structure.

Wet fluorescent method of magnetic particle testing utilizes a coil and central conductor test for locating indications in all directions. With the wet method extensive preparations are necessary. These preparations include controlling the liquid solution by either a catch basin or drain. The wet method requires access to both ends of small bores for cable connections to the current generator. To interpret the data obtained, a darkened area is required for a black light. Also due to the weight of the coil and conductor and to apply the magnetic particles suspension, the wet method reuires two men to perform the testing operation.

SUMMARY OF THE INVENTION

It is the purpose of this invention to provide an improved apparatus which is capable of inspecting relatively small blind bores, does not require extensive preparation for its use nor special liquid suspensions.

It is also a purpose of this invention to provide a relatively lightweight and easily manipulatable apparatus which is usable by a single operator.

The invention includes a portable frame on which adjustable electrical prods or contacts and a powder supply gun are carried in a single assembly. Prod tension against the wall of the bore being inspected is adjustable by varying spring plunger pressure. To accommodate the inspection of various sized bores the length of the prods are adjustable to provide good electrical contact with the bore wall. Powder is applied to the area under inspection with the power gun while current is flowing into the prods. To insure 100% coverage of the area under inspection, the powder gun nozzle can be rotated and retracted as necessary.

DESCRIPTION OF THE DRAWINGS

FIG. 1 is a view in elevation of the apparatus setup for radial inspection of a bore;

FIG. 2 is a view of the apparatus as it appears as viewed from the bottom in FIG. 1;

FIG. 3 is a view in elevation of the apparatus setup for linear inspection of a bore;

FIG. 4 is a view of the apparatus as it appears as viewed from the bottom of FIG. 3;

DESCRIPTION OF THE INVENTION

Figure 5:
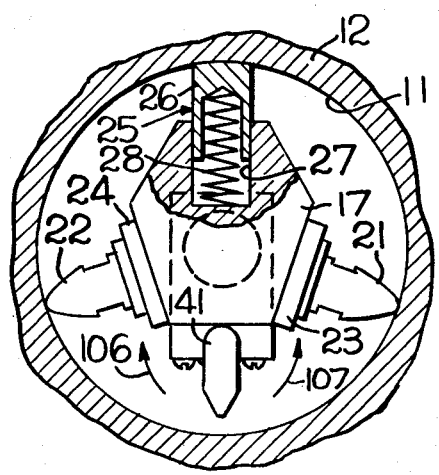
FIG. 5 is a transverse view of the apparatus taken in a plane represented by the line V—V in FIG. 1.

As shown in the drawings, a magnetic particle inspection apparatus 10 is disclosed and is set-up for radially inspecting the interior bore 11 of a workpiece 12. The apparatus 10 as depicted in FIGS. 1, 2, 5 and 6 includes a frame 16 which is herein illustrated as a tubular rod. At the forward or left-hand end of the rod 16, as viewed in FIGS. 1 and 2, the rod receives a prod head 17 having a clamp collar portion 18 which is adapted to be received on the end of the frame 16. A set screw 19 operates to secure the head in operative position.

The prod head 17 threadedly receives a pair of electrical contact prods 21 and 22. The prod contacts 21 and 22 are angularly disposed downwardly from the horizontal plane which passes through the longitudinal axes of the frame 16. Each of the contact prods 21 and 22 are electrically insulated from the prod head 17 by means of insulator washers 23 and 24, respectively.

Extending upwardly from the prod head 17 is a reaction member 25 comprising a positioning abutment or plunger 26. The plunger 26 is axially movable in a vertical plane in a bore 27 formed in the prod head 17. A spring 28 within the bore 27 serves to continuously urge the plunger 26 outwardly so as to be firmly engaged with the wall of the workpiece bore 11. With the prod head 17 disposed within the workpiece bore 11, the plunger 26 maintains the contact prods 21 and 22 in good electrical contact with the wall of the workpiece bore. The three point engagement of the prod head, by means of the prods 21 and 22 and the plunger 26, also stabilizes the end of the support within the bore 11 of the workpiece to facilitate placement and location of the pro head at the area to be inspected.

The tubular frame 16 is relatively long and its outer end or right-hand end as viewed in FIGS. 1 and 2, is provided with a horizontally extending handle 31 which is welded to the tubular frame 16. The handle 31 provides the means for facilitating the munipulation of the apparatus. Forwardly of the handle 31 is a pair of laterally extending cylindrical abutments 32 and 33 which are welded to the tubular support 16. The cylindrical abutments 32 and 33 give support and carry electrical supply cables 34 and 36 which are entrained over the cylindrical abutments. As shown, the electrical supply cables 34 and 36 extend forwardly towards the prod head 16 and are electrically connected to ends of a pair of copper links 37 and 38, respectively. The opposite ends of the copper links 37 and 38 are secured in electrical conducting engagement with the prods 21 and 22, respectively. Insulation of the links 37 and 38 from the prod head is accomplished by means of the insulator washers 23 and 24.

Below the tubular frame 16 there is provided a tubular particle powder supply pipe 41 which extends longitudinally parallel to the axis of the frame 16. At its inner end of the particle supply pipe 41 is turned downwardly 90° and flared as at 42 to provide a fan spread of particles on the adjacent wall of the workpiece bore 11. To secure the particle supply pipe 41 in operative position, the clamp collar 18 of the prod head 17 is provided with a depending bifurcated abutment 43 through which the pipe 41 extends. A plate clamp 44 is secured to the depending end surfaces of the bifurcated abutment and serves to hold the inner end of the pipe in parallel relationship to the frame 16 but still permitting rotation of the pipe. At its outer end the pipe is rotatably supported in a depending abutment 46 formed at the extreme outer end of the tubular frame 16. A bushing 47 carried by the abutment 46 and surrounding the supply pipe provides the necessary smooth surface for preventing abrasion of the supply pipe upon rotation thereof. A collar 48 secured around the supply pipe 41 between the flared end thereof and the abutment 43 is effective to prevent axial displacement of the pipe.

The apparatus 10 is operative to inspect areas transverse to the longitudinal axis. In order to effectively coat these areas, the particle spray tube is rotatable about its own axis. To enable the operator to effect such rotation while holding the apparatus in position, there is provided a particle or powder supply gun 53 which is conviently formed with a pistol like grip 54. The powder particle supply gun 53 is provided with an outlet port 56 which receives the powder supply tube 41.

The outlet 56 is internally connected within the gun 53 to a common supply hose 59 which is connected to a powder particle supply source (not shown). A control trigger 61 on the grip 54 is operatively connected to control the flow of powder particles to the outlet.

Figure 6:
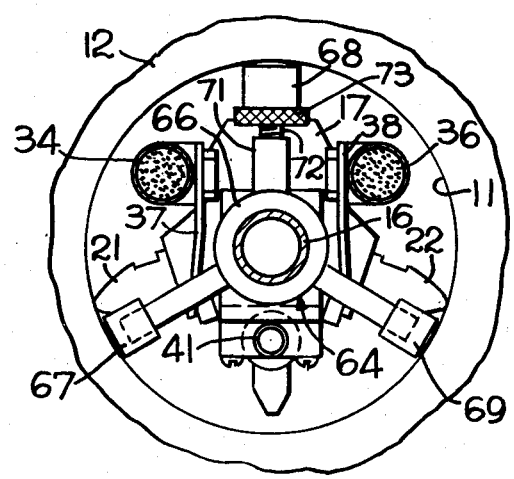
FIG. 6 is a transverse view of the apparatus taken in a plane represented by the line VI—VI in FIG. 1.
Figure 7:
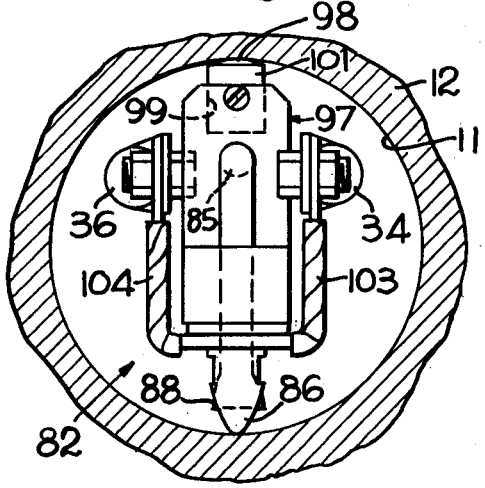
FIG. 7 is a transverse view of the apparatus taken in a plane represented by the line VII—VII in FIG. 3.
Figure 8:
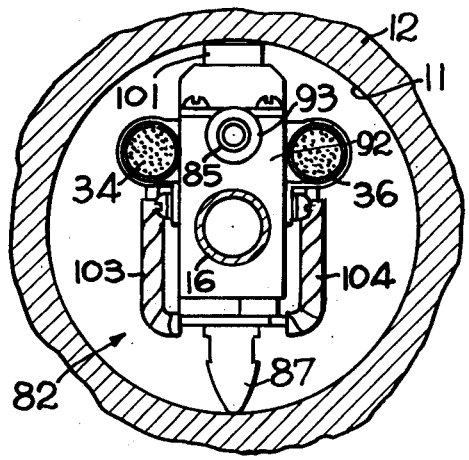
FIG. 8 is a transverse view of the apparatus taken in a plane represented by the line VIII—VIII in FIG. 3.

Inadvertent radial movement of the portion of the apparatus adjacent the bore opening would tend to displace the flared end 42 of the supply tube 41 from the area of the survey and is undesirable. To prevent inadvertent movement there is provided a three point stabilizing collar 64, as shown in FIGS. 1, 2 and 6. The stabilizing collar 64 includes a ring body portion 66 which is slidably fitted over the tubular frame 16 and presents three radially extending arms 67, 68 and 69 spaced 120° apart. The arm 68 is an adjustable member comprising an elongated internally threaded casing 71 integrally formed with the ring 66. A jack screw 72 threadedly engaged in the casing 71 can be conveniently moved axially by means of a knurled thumb member 73. Thus, the stabilizer 64 upon insertion into the bore 11 of the workpiece 12 can be firmly engaged with the wall of the bore 11.

As previously mentioned, an inspection is always made in two directions. The prod head 17 previously described provides capabilities for an inspection in a direction transverse to the axis of the bore 11. To effect an inspection of the bore wall in a direction parallel to the axis of the bore, a modified apparatus 80 is provided as shown in FIGS. 3, 4, 7 and 8. The apparatus 80 utilizes components of the apparatus 10. Thus, interchangeable components will be identified by the same reference numbers. As shown, the tubular frame 16 is utilized in an inverted position from its position in FIG. 1. A linear prod head 82 is secured to the inner end of the tubular frame 16. The prod head 82 includes a prod head support 83 which is mounted on the end of the tubular frame 16 and is secured thereto by cone pointed set screws 81. Extending forwardly from the prod head mount 83 is a carrier bar 84 in which a pair of electrical contact prods 86 and 87 are mounted in spaced apart relationship. A powder supply tube 85 connects with the outlet 56 of the powder supply gun 53 and extends forwardly to a position adjacent the forwardly positioned prod 86. The powder supply tube 85 at its forward end 87 is bent 90° with the outlet end thereof being flared as at 88 in a direction transverse to the axis of the bore 11. Thus, by moving the supply tube 85 longitudinally a relatively wide powder particle coating will be laid down. To permit such longitudinal movement of the pipe 85, the carrier 84 is provided with a longitudinally extending slot 89 through which the downwardly turned end 87 of the tube extends. The slot 89 is slightly wider than the diameter of the supply tube 85 so as to permit easy movement of the tube portion 87 within the slot and also to provide a guideway therefor. To facilitate the insertion of the powder supply tube 85 into an operative position, the slot 89 at the right-hand end thereof, as viewed in FIG. 4, is provided with an enlarged opening 91 which permits the flared end 88 of the tube to easily pass through. For guidably supporting the tube 85 the prod head support 83 extends upwardly as at 92 and formed with a slot in which a bushing 93 is craddled. A cap plate 94 operates to secure the bushing in position. Since the frame 16 is now inverted, the abutment 46 is pointed upwardly and presents the bushing 47 in axial alignment with the bushing 93. Thus, the supply pipe 85 which passes through both of the bushings 47 and 93 is guidably supported for longitudinal movement therein.

To insure good electrical contact of the prods 86 and 87 with the wall of the bore 11, there is provided a reaction member 97. The reaction member 97 is similar to the reaction member 25, shown in FIGS. 1 and 5. The reaction member 97 comprises an upwardly extending abutment 98 having a bore 99 in which a plunger 101 is disposed. A spring (not shown), similar to the spring 28 of FIG. 5, is carried within the bore 99 and operates to urge the plunger 101 outwardly against the wall of the bore 11. A reaction force is developed which reacts on the carrier bar 84 which in turn transmits the reaction force to both of the prods 86 and 87 urging them into good electrical contact with the wall of the bore 11.

The prods 86 and 87 are connected to the cables 36 and 34, respectively, by means of conducting links 103 and 104.

In operation the apparatus 10 is inserted into the bore 11 so as to position the prods 21 and 22 at the area to be inspected. The prods 21 and 22 are energized to establish a magnetic field between them. With the magnetic field stabilized, the operator applies the powder via the flared end 42 of the supply pipe 41 to the area by depressing the control button 61 in the gun handle. For a relatively wide spread inspection, transverses to the axis of the bore 11, the operator rotates the gun handle 53 back and forth which causes the flared end 42 of the powder supply pipe to oscillate back and forth as indicated by the arrows 106 and 107 in FIG. 5 to ensure 100% coverage of the powder over the area under inspection. In this manner, a relatively wide transverse inspection can be achieved. By rotating the apparatus bodily within the bore 11, in selected angular increments, the entire bore along a selected transverse path can be inspected. With respect to the linear apparatus 80, the transverse path inspected by the apparatus 10 can be linearly inspected by moving the supply pipe nozzle 88 across the path inspected by apparatus 10. Thus, by rotating the linear apparatus 80 in discrete increments, the entire transverse inspection can also be linearly inspected. A boroscope may be utilized to scan the area surveyed to obtain a visual interpretation of the inspection results.

The above-described apparatus provides a relatively simple device for effecting powder magnetic inspection of relatively small diameter bores and the apparatus is easily handled by a single operator and without undue preparation and chemicals.

The embodiments of the invention in which an exclusive property or privilege is claimed are defined as follows:

1. Apparatus for dry magnetic particle testing of blind bores of a workpiece;
   a frame;
   a prod head supported on said frame for movement with said frame;
   a pair of electrical contact prods carried by said prod head in spaced apart relationship and in position to engage with the wall of the bore upon insertion of the apparatus into a bore of a workpiece;
   means to electrically insulate said prods from said frame and from each other;
   yieldable means to urge said prods into pressure contact with the wall of the bore carried by said prod head and operatively positioned to engage the wall of the bore to develop a reaction force for urging said prods into pressure contact with the wall of the bore;
   a particle supply gun carried by said frame;
   a particle supply tube carried by said frame in position to direct particles to an area of the wall of the bore between said spaced apart prods, said particle supply tube being operatively connected to receive particles released by said gun;
   manual operable control means on said gun to effect a release of particles from said gun to said particle supply tube; and,
   separate electrical cables from a source of electrical energy connected to each of said electrical contact prods to energize them individually.

2. Apparatus according to claim 1 wherein said supply tube has its discharge end positioned adjacent the wall of the bore between said prods.

3. Apparatus according to claim 2 wherein the discharge end of said supply tube is formed as an ellipsoid with the major axis of the ellipsoid being parallel with the axis of the bore.

4. Apparatus according to claim 1 wherein there is provided an adjustable stabilizer means carried by said frame in position to engage the wall of the bore adjacent the entrance of the bore, said stabilizer being carried at the end of said frame closest to said particle supply gun.

5. Apparatus according to claim 1 wherein said frame is provided with a handle for manual manipulation of the apparatus by an operator.

6. Apparatus according to claim 5 wherein said supply tube extends rearwardly of said handle; and, said particle supply gun is connected to said supply tube at a position further from the entrance of the bore with respect to the position of said handle.

7. Apparatus according to claim 6 wherein there is provided means on said frame forwardly of said handle and operable to provide a support for said separate electrical cables and to confine said electrical cables between said means and said handle.

8. Apparatus according to claim 1 wherein said electrical contact prods are carried by said prod head in longitudinal spaced relationship in a manner so that said prods are in a line which is substantially parallel with the axis of the bore of the workpiece when said apparatus has been inserted into the bore.

9. Apparatus according to claim 8 wherein said particle supply tube has the end thereof which is remote from said particle supply gun turned and disposed in a position adjacent to the wall of the bore of the workpiece with its outlet being ellipsoid with its major axis disposed in a plane transverse to the plane in which the axis of the bore is located.

10. Apparatus according to claim 9 wherein said electrical contact prods are supported on a longitudinally extending carrier secured to the inner extending end of said frame, said carrier having a longitudinally extending guideway through which said particle supply tube extends; and,
    slide support means for guidably supporting said particle supply tube for axial movement relative to the frame;
    whereby the ellipsoidal end of said particle supply tube is maintained in substantially straight line of spray path of travel when said supply tube is moved axially.

11. Apparatus according to claim 10 wherein said contact prod carrier is provided with a yieldable force applying member disposed to engage the wall of the bore of the workpiece when the apparatus is in operative position within the bore, said yieldable force applying means urging said carrier in a direction to urge said contact prods in pressure contact with the wall of the base.

* * * * *